Figure 1:
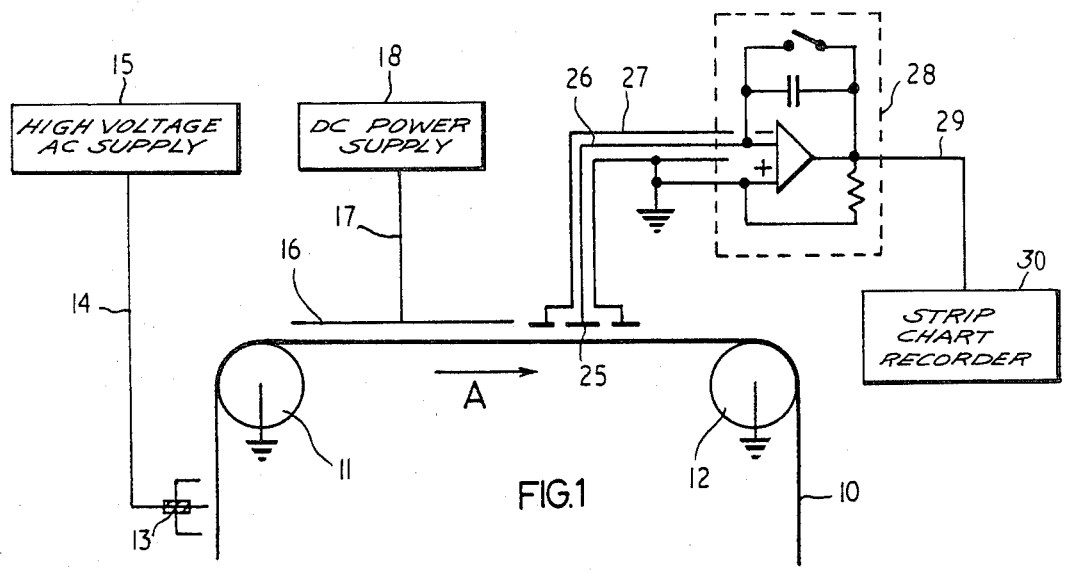

United States Patent [19]

Blythe

[11] 4,233,562
[45] Nov. 11, 1980

[54] APPARATUS AND METHOD FOR MONITORING WEB CONDUCTIVITY

[75] Inventor: Anthony R. Blythe, Welwyn, England

[73] Assignee: Imperial Chemical Industries Limited, London, England

[21] Appl. No.: 18,244

[22] Filed: Mar. 7, 1979

[30] Foreign Application Priority Data

Nov. 8, 1978 [GB] United Kingdom ............... 43733/78

[51] Int. Cl.³ ........................................... G01N 27/60
[52] U.S. Cl. .................................... 324/455; 324/452; 324/457
[58] Field of Search ................. 324/452, 455, 457, 458

[56] References Cited

U.S. PATENT DOCUMENTS

| 2,969,503 | 1/1961 | Bustin | 324/457 X |
| 3,234,462 | 2/1966 | Holdsworth | 324/458 X |
| 3,730,753 | 5/1973 | Kerr | 324/455 X |
| 3,944,354 | 3/1976 | Benwood et al. | 324/458 X |

FOREIGN PATENT DOCUMENTS

| 925319 | 3/1955 | Fed. Rep. of Germany | 324/455 |
| 491604 | 10/1938 | United Kingdom | 324/454 |

Primary Examiner—Alfred E. Smith
Assistant Examiner—Thomas P. O'Hare
Attorney, Agent, or Firm—Cushman, Darby & Cushman

[57] ABSTRACT

The invention provides an apparatus and method for monitoring the electrical conductivity of a web surface in which a forwardly moving web is exposed to an electrical field generated by a forwardly extending high voltage source so disposed adjacent the web as to induce a transverse redistribution of the electrical charges present on the web surface, the electrical field signal generated by the redistributed surface charges of opposite polarity to that of the source being monitored by a suitable field detector.

10 Claims, 3 Drawing Figures

APPARATUS AND METHOD FOR MONITORING WEB CONDUCTIVITY

This invention relates to a method and apparatus for monitoring the electrical surface conductivity of a moving web, and, in particular, of a moving plastics film.

The antistatic properties of a web, such as a plastics film, are dependent on the rate at which it will accumulate or dissipate and electrostatic charge. These properties influence the tendency of the web to attract and retain dust, and also its suitability for subsequent processing and handling on certain types of conversion and packaging equipment.

To improve the antistatic behaviour of a web, there may be incorporated into the web during production thereof appropriate additives which migrate to the web surface to provide an electrically conducting layer. Alternatively, an antistatic coating medium may be applied directly to the web surface, for example by a wash-coating technique. In either case it is desirable to have a continuous indication of the level of electrical surface conductivity achieved during the web production operation both to reduce the volume of quality control testing required to assess the acceptability of the finished product and to provide early warning of the development of any malfunction in the antistatic treatment technique.

Accordingly, the present invention provides a method of assessing the electrical conductivity of a surface of a moving web comprising feeding the web in a forward direction, exposing a surface of the moving web to an electrical field generated by a high voltage source extending in said forward direction and so disposed adjacent the web as to induce a redistribution, in a direction transverse to said forward direction, of the electrical charges present on that surface, and monitoring the electrical field signal generated by the redistributed surface charges of opposite polarity to that of the source.

The invention further provides an apparatus for assessing the electrical conductivity of a surface of a web travelling in a forward direction along a web path comprising an elongate electrode to be disposed adjacent the web path with the major axis of the electrode extending in said forward direction, a charging assembly to raise the electrode to an electrical potential sufficient to induce a redistribution, in a direction transverse to said forward direction, of the electrical charges present on the web surface, and an electrical field-sensitive detector assembly, disposed adjacent the web path of monitor the electrical field signal generated by the redistributed surface charges of opposite polarity to that of the electrode.

The technique of the invention depends, inter alia, on the redistribution of the electrical charges present on the web surface, under the influence of the field generated by the high voltage source or electrode, being sufficiently effective to generate an electrical field of adequate strength to activate the monitoring detector.

An approximate expression for the electrical field strength F incident upon the detector may be derived by consideration of an assembly comprising a pair of spaced-apart, electrically earthed, transporting rollers over which the web is fed in succession under sufficient tension to maintain the web in taut condition, the electrode and detector assembly being positioned adjacent the web between the rollers with the detector slightly downstream of the electrode in the direction of forward movement (the "machine" direction) of the web.

Assume that the flow of charge on the web surface, under the influence of the field generated by the electrode, occurs in a direction transverse to the machine direction, and ignore any flow of charge to the earthed rollers in the machine direction in view of the relatively long path lengths involved.

While the web is opposite the high voltage electrode the charge redistribution will develop in time as $(1-\exp(t_1/\tau))$, where $t_1$ is the residence time of the web opposite the electrode and $\tau$ is the RC time constant for the transverse flow of charge.

For a web velocity v, $t_1 = L/v$ where L is the length of the electrode.

For a web conductivity $\sigma$, $\tau = fC/\sigma$ where $1/C = 1/C_1 + 1/C_2$, $C_1$ and $C_2$ being the effective capacitances coupling the web to the electrode and earth, respectively, and f is a geometrical factor relating to the spatial distribution of the capacitances to the web.

In the interval between the web passing from the high voltage electrode to the detector the charge distribution will have decayed by the factor $\exp(-t_2/\tau)$, where $t_2 = g/v$ is the time taken for the web to cross the gap g between the end of the electrode and the detector.

Taking these time factors into account, the expression for the field incident on the detector becomes:

$$F = \frac{V}{d} \frac{C_2}{C_1 + C_2} (1 - e^{-L\sigma/vfC}) e^{-g\sigma/vfC},$$

where V is the voltage on the high voltage electrode and d is the separation of the high voltage electrode from the web.

From the above expression it is evident that the detector signal will increase as the distance d between the high voltage electrode and the web is decreased. An appropriate separation bewteen web and electrode is readily established by simple experimentation. In practice, it is preferred that the separation should not be significantly less than about 10 mm to avoid contact between the electrode and web as the latter travels along its forward path.

Similarly, the detector signal will increase as the gap g between the high voltage electrode and a detector (located downstream thereof, and on the same side of the web) is decreased. Preferably, to ensure effective isolation of the electrode from the detector the gap therebetween is not reduced below about 10 mm.

The residence time of a particular zone of the web opposite the high voltage electrode should be sufficient to allow an adequate transverse redistribution of charge on that zone of the web surface to occur before the web passes to the detector. Establishment of an appropriate residence time is readily achieved for a web of a particular material by simple experimentation on the web in question. In general, the residence time is conveniently of the order of 0.25 seconds, preferably between 0.5 and 1 second or greater. Web speed may vary over a wide range depending, inter alia, on the nature of the web—for example, from about 0.5 to 10 meters/second in the case of a polyolefin film web, and to ensure the achievement of adequate residence time at high web speeds the high voltage electrode is suitably extended in the machine direction. For a polyolefin film travelling at a line speed of about 1 ms$^{-1}$ an electrode length of from about 0.5 to 1.5 meters, giving a residence time of from 0.5 to 1.5 seconds, has been observed to create a field of acceptable strength at the detector.

The voltage supplied to the long electrode should be sufficiently high to generate an acceptable signal at the detector. Generally, a high voltage within a range of from about 0.1 to about 10 kV, preferably from about 0.3 to 3 kV to reduce the incidence of corona discharge on the web, is acceptable. The high voltage may be generated by conventional sources, e.g. a DC source such as a battery or a stabilised DC power supply (e.g. Brandenburg), or an appropriate AC supply. If an AC source is employed the periodic time of the high voltage should be comparable to or greater than the time constant for redistribution of the charge on the web, and AC amplification methods may be incorporated in the detector assembly.

The electrode extends in the direction of travel of the web and may be of any convenient form such as a rod or bar, but preferably is in the form of a rectangular plate, positioned with a major planar face thereof substantially parallel to the web path. The electrode is conveniently fabricated from aluminum or an alloy thereof.

The detector assembly comprises a probe, e.g. in the form of a rectangular plate, suitably positioned to receive the electrical field signal generated by the change in charge density on the web surface, the probe being electrically screened and linked to a monitor such as an electrometer operating in a charge measurement mode. The electrometer however may experience drift problems necessitating periodic re-zeroing of the electrometer, and alternative monitoring systems, such as a field mill, may be employed, if desired. As hereinafter described, a phase-sensitive detector may additionally be employed to monitor an alternating field signal.

If desired the magnitude of the field signal received by the monitor may be displayed, for example in digital form on a visual display unit, or on a conventional strip chart recorder.

The signal-to-noise ratio of the system of the invention should be as high as possible, for example, at least 10:1, and may be improved, if desired, by periodically "chopping", i.e. switching on and off or alternating the sign of, the high voltage supply to the electrode, suitably at a frequency of about 1 Hz. Such an arrangement necessitates the use of a phase-sensitive detector to monitor the redistribution of charge on the web surface with reference to the changing high voltage.

The invention is hereinbefore described in terms of a system wherein the detector assembly is positioned downstream of the high voltage electrode in the machine direction and on the same side of the web, but it will be appreciated that the detector may be located on the opposite side of the web from the high voltage electrode at or adjacent the downstream end thereof—either with a gap g between the electrode and detector of similar magnitude to that hereinbefore described or with the detector positioned marginally upstream of the downstream end of the electrode. In the latter case the detector is exposed to an electrical field comprising a component received directly through the web from the high voltage electrode in addition to that generated by the redistributed charge on the web surface. The arrangement of the high voltage electrode and detector on the same side of a web is clearly advantageous in that it provides a non-contacting monitoring device all components of which can be located on the same side of a web, and in which, for a conductive web, a distinct field signal, of opposite polarity to that of any stray signal emanating from the electrode, is received at the detector.

In practice it is desirable to monitor conductivity across the width of a web, and this may be achieved by spacing a limited number of high voltage electrodes and associated detector assemblies transversely of the web surface. However, unless the transverse spacing of these assemblies is adequate, for example one assembly for about each 800 mm width of web, mutual interference is likely to occur and spurious signals will be generated. This may be overcome by sequential switching of the high voltage to each of the transversely spaced electrodes in turn, or by employing an alternate positive and negative high voltage on adjacent electrodes, but an alternative and preferred approach is to employ a traversing assembly whereby a single high voltage electrode and its associated detector slowly scans across the width of the web.

The presence on the web surface of a high net charge, for example—of the order of 500 $nCm^{-2}$, may interfere with the conductivity monitoring technique of the invention. Such charges may be eliminated from the web surface by conventional means—for example by a high voltage static eliminator (e.g. Meech) operating upstream of the high voltage electrode of the conductivity monitoring device.

The technique of the invention is suitably employed in assessing the electrical surface conductivity of a variety of webs including paper, paperboard, cellulosic films, polymeric films, and laminates thereof. Typical polymeric films include oriented, particularly biaxially oriented, films formed in conventional manner from polyesters such as polyethylene terephthalate and polyethylene-1,2-diphenoxyethane-4,4'-dicarboxylate, and from polymers and copolymers of 1-olefins such as ethylene, propylene, butene-1, and 4-methylpentene-1, particularly a film formed from a high molecular weight stereoregular predominantly crystalline polymer of propylene, either in the form of a homopolymer or copolymerised with minor quantities (e.g. up to 15% by weight of the copolymer) of at least one other unsaturated monomer, such as ethylene). The technique is also suitable for assessing the electrical conductivity of multiple-layer films, such as a polypropylene substrate having on at least one surface thereof a layer comprising a copolymer of propylene (80 to 95% by weight) with another alpha-olefin containing from 4 to 10 carbon atoms, such as butene-1.

Webs to be monitored according to the invention may have been subjected to conventional web-processing techniques. For example, an oriented polymeric film may be "heat-set", i.e. dimensional stability of the film is improved by heating the film, while restrained against thermal shrinkage, to a temperature above the glass transition temperature of the polymer from which the film is formed but below the melting point thereof. Likewise, the film may have been exposed to surface treatments, such as a corona discharge treatment to improve bonding and print receptivity. Antistatic and-/or other additives may be present in the film or applied to the surface thereof—for example by a wash coating technique.

The technique of the invention is particularly suitable for monitoring films with a relatively low electrical surface conductivity—for example, between 1 and 1000 pS, and particularly between about 10 and 200 pS.

The system of the invention may be employed to monitor relative changes in electrical surface conductivity, or, if desired, the equipment may be calibrated with webs of standard characteristics, to provide an absolute measure of electrical surface conductivity.

Forwarding of a web in the machine direction through an assembly of the kind described is conveniently effected by conventional web-handling equipment—for example, by means of turner bars or perforated gas-bearings over which the web is passed. Conventional rotatable supporting rolls with appropriate electrical connection to Earth have proved particularly suitable.

Polymeric films to be monitored according to the invention may vary considerably in thickness but preferably are within a thickness range of from 2 to 150 microns.

Figure 2:
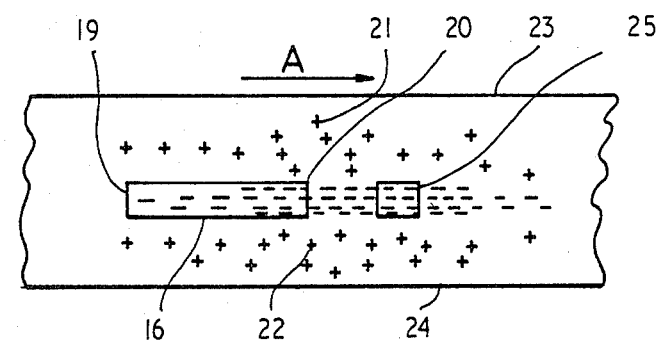
Figure 3:
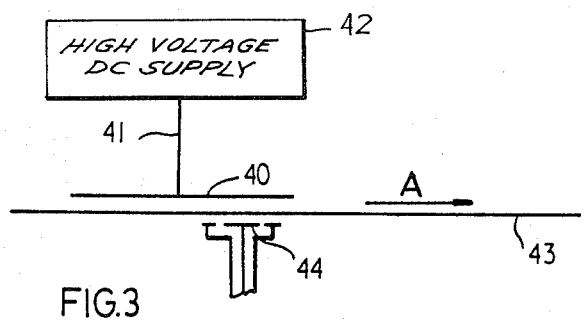

The invention is illustrated by reference to the accompanying drawings in which:

FIG. 1 is a schematic elevation of a web monitoring assembly and associated electrical circuit diagram, FIG. 2 is a plan view of the monitored web, and FIG. 3 is a schematic elevation of a monitoring assembly in which the electrode and detector units are at opposite surfaces of the web.

Referring to FIG. 1 of the drawings, a polymeric film web 10 is shown travelling in the forward or machine direction (arrow A) in taut condition between a pair of spaced-apart guide rollers 11, 12 each of which is maintained at earth potential.

On the upstream side of roller 11 the dynamic charge level on the web surface is reduced by exposure of the web to the action of a static eliminator 13 coupled by electrical leads 14 to a high voltage AC supply 15 suitably operating at a potential of from about 6 to 12 kilovolts (rms).

Immediately downstream of roller 11 the web is exposed to an electrode plate 16 extending in the machine direction adjacent, and in a plane substantially parallel to, web 10, and coupled through electrical leads 17 to a stabilised DC power supply 18 maintained at a high positive electrical potential—for example, of the order of 3 kV. (Alternatively, the high voltage may be negative in sign, the induction effects being reversed.) As the web passes progressively beneath electrode 16 a redistribution of the charges present on the web surface occurs, the negative charges being attracted transversely across the web surface (i.e. in a plane normal to that embracing FIG. 1) to the zone beneath positive electrode 16 to leave a distributed positive charge at the outer zones of the web surface. The movement of charge on the web surface is illustrated schematically in FIG. 2 of the drawings, the web surface being effectively electrically neutral as the web, moving in the direction of arrow A, approaches positive high voltage electrode 16. As web 10 passes downstream of the leading edge 19 of electrode 16, negative charges are drawn across the web surface to the area beneath electrode 16, the density of the negative charge cloud increasing as the web progresses to the trailing edge 20 of the electrode leaving corresponding zones 21, 22 of positive charges in the vicinity of the longitudinal edges 23, 24 of the web.

Downstream of trailing edge 20 of electrode 16, and before significant decay of the dense cloud of negative charges on the web surface occurs, the electrical field generated by the negative charge cloud is monitored by a plate detector 25 aligned with electrode 16 adjacent, and in a plane substantially parallel to, web 10. The field signal received at detector plate 25 is fed therefrom along electrical leads 26 within an earthed electrical screen 27 to an electrometer amplifier generally designated 28, the amplified signal being subsequently fed along electrical lead 29 for display on a strip chart recorder 30.

In an alternative arrangement illustrated in FIG. 3, a longitudinal electrode 40 coupled through leads 41 to a stabilised high voltage DC power supply 42 is located adjacent, and substantially parallel to, one surface of a forwardly moving web 43, with a screened detector plate 44 located at the other surface of the web opposite the downstream end 45 of electrode 40. This system operates in a manner similar to that of FIG. 1, the signal received at detector plate 44 being fed to a suitable amplifier/display assembly (not shown).

The electrode/detector assembly, as hereinbefore described, may reciprocate back and forth across the web surface with an appropriate cycle time to monitor electrical surface conductivity across the entire web surface.

The invention is further illustrated by reference to the following Examples.

EXAMPLE 1

The technique of the invention was employed to monitor the electrical surface conductivity of an oriented, heat-set polypropylene film of about 25 $\mu$m thickness, the film having a surface layer comprising a propylene-butene-1 random copolymer. The film was prepared by a tubular process similar to that disclosed in British Pat. No. 1,284,321, and an aqueous antistatic coating solution comprising glycerol, choline chloride and an amine sulphate was applied to the external surface of the film tube prior to orientation thereof.

On emerging from a matt-surfaced roller heat-setting assembly of the kind described in British Pat. No. 1,124,886 the film was fed through an assembly of the kind shown in FIG. 1 of the accompanying drawings, the surface of the film having the antistatic wash-coating thereon being adjacent the electrode and detector assembly.

The high voltage electrode of the monitoring equipment was in the form of a rectangular aluminium plate 200 mm wide and 1 meter long (in the machine direction), and was positioned in a plane substantially parallel to the film at a distance of about 10 mm therefrom. Downstream of the electrode was positioned a square aluminium sensor plate of side 150 mm, also in a plane substantially parallel to the film surface and at a distance of about 10 mm therefrom. The gap between the high voltage electrode and sensor plate was about 25 mm.

A DC voltage of +3 kV was applied to the electrode and the sensor plate was coupled to a DC negative feedback electrometer detector.

At a linear film speed of 1.3 ms$^{-1}$ a mean field signal of $-60$ kVm$^{-1}$ was received at the detector.

When application of the aqueous antistatic solution was discontinued the signal received at the detector was about $+10$ kVm$^{-1}$, indicating that a stray field of this magnitude from the high voltage electrode was being picked up by the detector.

When application of the aqueous antistatic solution to the film surface was restarted, the mean field signal at the detector returned to $-60$ kVm$^{-1}$, and fell to zero when the high voltage supply to the electrode was switched off.

After passing through the monitor assembly the film was wound up on to a mill reel for storage. The electrical surface conductivity of samples of film from this reel was measured by means of a simple apparatus comprising a DC power supply of 70 volts in series with an electronic microammeter and with an electrode assembly comprising a pair of knife edged electrodes each of 100 mm length and spaced-apart in parallel by a distance of 0.25 mm. To measure surface conductivity of the film, the electrode assembly was placed on a film sample thereby completing an electrical circuit through the apparatus. The mean conductivity recorded by the microammeter of the film samples was 100 pico Siemens (pS).

EXAMPLE 2

The procedure of Example 1 was repeated save that the size of the high voltage electrode plate was reduced to 200 mm wide and 0.5 m long.

A mean field signal of $-50$ kVm$^{-1}$ was received at the detector with a linear film speed of 1.3 ms$^{-1}$.

EXAMPLE 3

The procedure of Example 2 was repeated save that the voltage applied to the electrode was $+6$ kV DC.

The mean field signal received at the detector was $-110$ kVm$^{-1}$.

EXAMPLE 4

The procedure of Example 3 was repeated save that the voltage applied to the electrode was reduced to $-300$ V DC.

The mean field signal received at the detector was $+6.5$ kVm$^{-1}$.

EXAMPLE 5

The procedure of Example 1 was repeated save that:
(a) the film speed was increased to 1.4 ms$^{-1}$,
(b) the dimensions of the electrode plate were 200 mm wide and 750 mm long,
(c) the voltage applied to the electrode was $+2.5$ kV DC,
(d) the electrometer was replaced by a Precision field mill, Model 92, supplied by Industrial Developments Bangor (UCNW), the mill having a circular sensing aperture of 65 mm diameter,
(e) the gap between the downstream end of the electrode plate and the centre of the sensing aperture of the field mill was 50 mm.

The mean field signal received by the field mill was $-130$ kVm$^{-1}$, and samples of the film from the resultant mill reel, when examined with the simple microammeter assembly described in Example 1, exhibited a surface conductivity of 150 pS.

I claim:

1. A method of assessing the electrical conductivity of a surface of a moving web comprising feeding the web in a forward direction, generating an electrical field by supplying a high voltage to an electrode extending in said forward direction and disposed adjacent the web, exposing said surface of the moving web to said electrical field so as to induce a redistribution, in a direction transverse to said forward direction, of the electrical charges present on that surface, whereby an electrical field signal is generated by the redistributed surface charges of opposite polarity to that of the electrode, and monitoring said electrical field signal.

2. A method according to claim 1 wherein the residence time of any zone of the web opposite said electrode is from 0.25 to 1.5 seconds.

3. A method according to claim 1 including the step of periodically chopping the high voltage supply to said electrode.

4. A method according to claim 1 wherein the electrode traverses said web surface.

5. A method according to claim 1 wherein the electrical surface conductivity of the web is from 1 to 1000 pico Siemens.

6. A method according to claim 1 wherein the web is an oriented polyolefin film.

7. An apparatus for assessing the electrical conductivity of a surface of a web travelling in a forward direction along a web path, said apparatus comprising an elongate electrode to be disposed adjacent the web path with the major axis of the electrode extending in said forward direction, a charging assembly to raise the electrode to an electrical potential sufficient to induce a redistribution, in a direction transverse to said forward direction, of the electrical charges present on the web surface, and an electrical field-sensitive detector assembly, disposed adjacent the web path to monitor the electrical field signal generated by the redistributed surface charges of opposite polarity to that of the electrode.

8. An apparatus according to claim 7 wherein the detector assembly comprises a field mill.

9. An apparatus according to claim 7 wherein the electrode and detector assembly are disposed adjacent the same surface of said web.

10. An apparatus according to claim 7 including a traversing assembly to scan the electrode and detector assembly across the surface of said web.

* * * * *